(12) United States Patent
Bevill et al.

(10) Patent No.: US 10,098,859 B2
(45) Date of Patent: Oct. 16, 2018

(54) COCRYSTALS OF P-COUMARIC ACID

(71) Applicant: AMRI SSCI, LLC, West Lafayette, IN (US)

(72) Inventors: Melanie Janelle Bevill, West Lafayette, IN (US); Nate Schultheiss, Kingwood, TX (US)

(73) Assignee: AMRI SSCI, LLC, West Lafayette, IN (US)

( * ) Notice: Subject to any disclaimer, the term of this patent is extended or adjusted under 35 U.S.C. 154(b) by 0 days.

(21) Appl. No.: 14/017,879

(22) Filed: Sep. 4, 2013

(65) Prior Publication Data

US 2014/0073674 A1  Mar. 13, 2014

Related U.S. Application Data (60) Provisional application No. 61/696,900, filed on Sep. 5, 2012.

(51) Int. Cl.
*C07D 213/56* (2006.01)
*A61K 31/465* (2006.01)
*A61K 31/192* (2006.01)
*C07D 213/82* (2006.01)

(52) U.S. Cl.
CPC .......... *A61K 31/192* (2013.01); *A61K 31/465* (2013.01); *C07D 213/82* (2013.01)

(58) Field of Classification Search
CPC ........................... C07D 213/56; A61K 31/465
USPC .......................................... 546/316; 514/355
See application file for complete search history.

(56) References Cited

U.S. PATENT DOCUMENTS

| | | |
|---|---|---|
| 7,452,555 B2 | 11/2008 | Childs |
| 8,193,363 B2 | 6/2012 | Bjork et al. |
| 8,212,079 B2 | 7/2012 | Childs |
| 8,318,943 B1 | 11/2012 | Sun et al. |
| 8,324,389 B2 | 12/2012 | Hashash et al. |
| 8,350,085 B2 | 1/2013 | Childs |
| 8,513,236 B2 | 8/2013 | Schultheiss et al. |
| 8,653,274 B2 | 2/2014 | Bjork et al. |
| 8,772,496 B2 | 7/2014 | Chen |
| 8,791,140 B2 | 7/2014 | Campeta et al. |
| 8,927,771 B2 | 1/2015 | Miller et al. |
| 9,029,369 B2 | 5/2015 | Holland et al. |
| 9,096,530 B2 | 8/2015 | Matzger et al. |
| 9,120,766 B2 | 9/2015 | Bevill et al. |
| 9,314,459 B2 | 4/2016 | Bevill et al. |
| 2011/0251426 A1 | 10/2011 | Childs et al. |
| 2013/0102781 A1 | 4/2013 | Bevill et al. |
| 2014/0073674 A1 | 3/2014 | Bevill et al. |
| 2014/0235595 A1 | 8/2014 | Albert et al. |
| 2015/0216851 A1 | 8/2015 | Bevill et al. |

OTHER PUBLICATIONS

Ivanisevic et al., "Use of X-ray . . . " Pharm. Sci. Encycl. p. 1-42 (2010).*
Ivanisevic et al., "Uses of X-ray, etc.," Pharm. Form. Qual. 2011, pp. 30-33.*
Bhattacharya et al., "Thermoanalytical and Crystallographic Methods" in Brittain H. ed., $2^{nd}$ ed. Informa Healthcare:NY 2009 p. 318-335.*
Aakeroy, "Crystal Engineering, etc.," Acta Cryst. (1997) B53, 569-586.*
Sekhon BS, "Pharmaceutical co-cyrstals, etc." Ars Pharm., 50(2): 99-117 (2009).*
Kirk-Othmer Encyclopedia of Chemical Technology, 8, pp. 95-147 (2002).*
Halebian et al., Pharmaceutical Applications, etc., Pharmaceutical Sciences 58(8), 1969, 911-929.*
Bernstein, "Polymorphism in . . . " p. 115-118, 272 (2002).*
Stahly, "Diversity in Single—, etc.", Crystal Growth & Design, 7 (6), 2007, 1007-1026.*
Vippagunta et al., "Crystalline Solids", Advanced Drug Delivery Reviews 48 (2001) 3-26.*
Braga et al., "Making crystals from . . . " J. Royal Soc. Chem. Commun. p. 3635-3645 (2005).*
Davidovich et al., "Detection of polymorphism . . . " Am. Pharm. Rev. v.&(1) p. 10, 12, 14, 16, 100 (2004).*
Dean "Analytical Chem . . . " p. 10.24-10.26 (1995).*
Seddon "Pseudopolymorph . . . " Crystal Growth & design v.4(6) p. 1087 (2004) (2 pages from internet).*
Ravikumar et al., "Structural, spectroscopic, etc.," J of Molecular Structure 1033 (2013) 272-279.*
Dunitz "Crystal, etc.," CrystEngComm, 2003, 5(91), 506.*
Childs et al., "The Salt-Cocrystal, etc.," Molecular Pharmaceutics, 2007, 4(3), 323-338.*
Weyna et al., "Synthesis and, etc.," Crystal Growth & Design, 2009, 9(2) 1106-1123.*
Fleischman et al., "Crystal Engineering, etc.," Crystal Growth & Design, 2003, 3(6), 909-919.*
Orola et al., "Nicotinamide, etc.," CrystEngComm, 2009, 11, 415-417.*
Bevull et al., "Polymorphic, etc.," Cryst. Growth Des., 2014, 14, 1438-1448.*
Rodriguez-Hornedo et al., "Reaction, etc.," Molecular Pharmaceutics, 3(3) 362-367.*
David C. Lee and Michael L Webb, Pharmaceutical Analysis, 2003, pp. 254-259, 1st edition, CRC Press, Boca Raton, Florida, United States of America.
Nate Schultheiss, et al, Cocrystals of nutraceutical p-coumaric acid with caffeine and theophylline: polymorphism and solid-state stability explored in detail using their crystal graphs, CrystEngComm, Sep. 22, 2010, pp. 611-619, 13, The Royal Society of Chemistry, London, United Kingdom.
United States Patent and Trademark Office, Non-Final Office Action for U.S. Appl. No. 13/657,259, Jul. 24, 2014, Alexandra, Virginia.
Bevill et al., "Polymorphic Cocrystals of Nutraceutical Compound p-Coumaric Acid with Nicotinamide: Characterization, Relative Solid-State Stability, and Conversion to Alternate Stoichiometries," Cryst. Growth Des., pp. 1438-1448 (2014).
Bevill et al., "Phase Diagrams Illustrating Solubility and Gibb's Free Energy of 1:1 and 2:1 Cocrystals of Nutraceutical p-Coumaric Acid with Nicotinamide," Poster, AAPS Meeting (2012).

(Continued)

*Primary Examiner* — Patricia L Morris
(74) *Attorney, Agent, or Firm* — LeClairRyan PLLC (57) ABSTRACT

Disclosed herein are cocrystals of p-coumaric acid and nicotinamide. A 1:1 molar ratio and a 2:1 molar ratio of p-coumaric acid to nicotinamide are herein disclosed.

11 Claims, 9 Drawing Sheets

(56) References Cited

OTHER PUBLICATIONS

Bevill et al., "Phase Diagrams Illustrating Solubility and Gibb's Free Energy of 1:1 and 2:1 Cocrystals of Nutraceutical p-Coumaric Acid with Nicotinamide," Abstract ID: AM-12-02982 (Jun. 8, 2012).

Etter, Margaret C. et al., "Graph-Set Analysis of Hydrogen-Bond Patterns in Organic Crystals," Acta Cryst., B46, pp. 256-262 (1990).

Etter, Margaret C. et al., "The Use of Cocrystallization as a Method of studying Hydrogen Bond Preferences of 2-Aminopyridine," Journal of the Chemical Society, Chemical Communications, No. 8, pp. 589-591 (1990).

Flack, H.D., "On Enantiomorph-Polarity Estimation," Acta Cryst., A39, pp. 876-881 (1983).

Gorbitz, C.H., "On the inclusion of solvent molecules in the crystal structures of organic compounds," Acta Cryst., B56, pp. 526-534 (2000).

Hooft R.W.W. et al., "Determination of absolute structure using Bayesian statistics on Bijvoet differences", J. Appl. Cryst., vol. 41, pp. 96-103 (2008).

Kumar et al., "Molecular Complexes of Some Mono- and Dicarboxylic Acids with trans-1,4-Dithiane-1,4-dioxide," American Chemical Society, Crystal Growth & Design, vol. 2, No. 4, pp. 313-318 (2002).

Schultheiss, N. et al., "Nutraceutical cocrystals: utilizing pterostilbene as a cocrystal former," Crystal Engineering Communications, vol. 12, pp. 2436-2442 (2010).

Schultheiss, N. et al., "Attempted construction of minoxidil: carboxylic acid cocrystals; 7 salts and 1 cocrystal resulted," Crystal Engineering Communications, vol. 12, pp. 742-749 (2010).

Schultheiss, N. et al., "Attempted construction of minoxidil: carboxylic acid cocrystals; 8 salts and 1 cocrystal resulted," Crystal Engineering Communications, Supplementary Material, pp. 1-19 (2010).

Schultheiss, N. et al., "Nifedipine-pyrazine (211)," Acta Cryst. E66, pp. 2297-2298 and Sup-1 to Sup-9 (2010).

United States Patent and Trademark Office, Non-Final Office Action for U.S. Appl. No. 13/657,259, dated Jul. 24, 2014.

Wolfe et al., "Polymorphic Cocystals" Poster, AAPS Meeting (2010).

Breuil, A.C. et al., "Characterization of a Pterostilbene Dehydromer Produced by Laccase of Botrytis cinerea", Phytopathology vol. 89, No. 4, pp. 298-302 (1999).

Pezet, R., "Purification and characterization of a 32-kDa laccase-like stilbene oxidase produced by Botrytis cinerea Pers.:Fr," FEMS Microbiology letters, vol. 167, pp. 203-208 (1998).

Ivanisevic et al., "Uses of X-Ray Powder Diffraction in the Pharmaceutical Industry", Pharmaceutical Sciences Encyclopedia: Drug Discovery, Development, and Manufacturing, pp. 1-42 (2010).

Barash, Eyal, Enablement Standards Under MPEP 2164, submitted in advance of an Examiner's Interview of U.S. Appl. No. 14/017,879.

USPTO, U.S. Patent Application Publication No. 2014/0073674-A1, Mar. 13, 2014.

U.S. CAFC, *Smithkline Beecham Corp* v. *Apotex,* Apr. 23, 2004.

Kaur et al., Do carboximide-carboxylic acid combinations form co-crystals?, International Union of Crystallography Journal, Feb. 7, 2015, p. 341-351, 2, Chester, England.

* cited by examiner

COCRYSTALS OF P-COUMARIC ACID

This application claims priority to U.S. Provisional Application No. 61/696,900, filed on Sep. 5, 2012, which is incorporated herein by reference in its entirety The invention relates to novel cocrystals of p-coumaric acid and nicotinamide, pharmaceutical compositions comprising the novel cocrystals, methods of making the cocrystals, and methods of using the cocrystals.

BACKGROUND

P-coumaric acid is a phytochemical and nutraceutical and is commonly found in various edible plants such as peanuts, tomatoes, and carrots. Promising pharmacokinetic studies with p-coumaric acid have shown it to have a positive response in protection against colon cancer on cultured mammalian cells. Other studies have shown it to have anti-inflammatory and antioxidant properties in animals. Nicotinamide is the amide of nicotinic acid and is a water-soluble vitamin. Nicotinamide has anti-inflammatory properties and is used in the treatment of acne.

The structures of p-coumaric acid and nicotinamide are shown below:

P-coumaric acid      Nicotinamide

Cocrystals of p-coumaric acid have previously been published. For example, cocrystals with caffeine and theophylline have previously been described (Cryst. Eng. Comm. 2011, 13 611-19). Likewise, cocrystals containing nicotinamide have been reported.

A cocrystal of a compound is a distinct chemical composition between the compound and coformer, and generally possesses distinct crystallographic and spectroscopic properties when compared to those of the compound and coformer individually. A coformer is also a compound and is often referred to as a "guest". The compound which is not the coformer is often referred to as the "host." Unlike salts, which possess a neutral net charge, but which are comprised of charge-balanced components, cocrystals are comprised of neutral species. Thus, unlike a salt, one cannot determine the stoichiometry of a cocrystal based on charge balance. Indeed, one can often obtain cocrystals having molar ratios of compound to coformer of greater than or less than 1:1. The molar ratio of the components is a generally unpredictable feature of a cocrystal.

Cocrystals have the potential to alter physicochemical properties. More specifically, cocrystals have been reported to alter aqueous solubility and/or dissolution rates, increase stability with respect to relative humidity, and improve bioavailability of active pharmaceutical ingredients with respect to other cocrystals of such ingredients. The coformer, or guest, is often varied or selected for purposes of altering such properties.

The chemical composition of a cocrystal, including the molar relationship between the coformer and the compound (such as an API) can be determined by single crystal x-ray analysis. Where such an analysis is not available, often solution-state proton NMR is used to verify composition and identify molar ratio.

Cocrystal formation may be further confirmed by comparing solid-state analytical data of the starting materials with the corresponding analytical method collected of the cocrystal. Data from a cocrystal will be represented by an analytical response that is not simply a linear superposition of the starting materials. For example, x-ray powder diffraction (XRPD) may be used for such comparison and the XRPD pattern of a cocrystal will differ from that of a physical mixture of the starting materials. Single crystal studies can confirm solid-state structure. In a cocrystal, the compound and the coformers each possess unique lattice positions within the unit cell of the crystal lattice. Additionally, indexing may be used to confirm the presence of a single phase.

A single crystal structure is not necessary to characterize a cocrystal. Other solid-state analytical techniques may be used to characterize cocrystals. Crystallographic and spectroscopic properties of cocrystals can be analyzed with XRPD, Raman spectroscopy, infrared spectroscopy, and solid-state $^{13}$C NMR spectroscopy, among other techniques. Cocrystals often also exhibit distinct thermal behavior compared with other forms of the corresponding compound. Thermal behavior may be analyzed by such techniques as capillary melting point, thermogravimetric analysis (TGA), and differential scanning calorimetry (DSC) to name a few. These techniques can be used to identify and characterize the cocrystals.

For example, the entire XRPD pattern output from a diffractometer may be used to characterize a cocrystal. A smaller subset of such data, however, may also be suitable for characterizing a cocrystal. For example, a collection of one or more peaks from such a pattern may be used to characterize a cocrystal. Indeed, even a single XRPD peak may be used to characterize a cocrystal. Similarly, subsets of spectra of other techniques may be used alone or in combination with other analytical data to characterize cocrystals. In such examples of characterization as provided herein, in addition to the x-ray peak data, one also is able to provide the identity of the guest and host of the cocrystal and, often, their respective molar ratio as part of the characterization.

An XRPD pattern is an x-y graph with °2θ (diffraction angle) on the x-axis and intensity on the y-axis. These are the peaks which may be used to characterize a cocrystal. The peaks are usually represented and referred to by their position on the x-axis rather than the intensity of peaks on the y-axis because peak intensity can be particularly sensitive to sample orientation (see Pharmaceutical Analysis, Lee & Web, pp. 255-257 (2003)). Thus, intensity is not typically used by those skilled in the pharmaceutical arts to characterize cocrystals.

As with any data measurement, there is variability in x-ray powder diffraction data. In addition to the variability in peak intensity, there is also variability in the position of peaks on the x-axis. This variability can, however, typically be accounted for when reporting the positions of peaks for purposes of characterization. Such variability in the position of peaks along the x-axis derives from several sources. One comes from sample preparation. Samples of the same crystalline material, prepared under different conditions may yield slightly different diffractograms. Factors such as particle size, moisture content, solvent content, and orientation may all affect how a sample diffracts x-rays. Another source of variability comes from instrument parameters. Different x-ray instruments operate using different parameters and these may lead to slightly different diffraction patterns from the same crystalline cocrystal. Likewise, different software packages process x-ray data differently and this also leads to variability. These and other sources of variability are known to those of ordinary skill in the pharmaceutical arts.

Due to such sources of variability, it is common to recite x-ray diffraction peaks using the word "about" prior to the peak value in °2θ which presents the data to within 0.1 or 0.2°2θ of the stated peak value depending on the circumstances. All x-ray powder diffraction peaks cited herein are reported with a variability on the order of 0.2°2θ and are intended to be reported with such a variability whenever disclosed herein whether the word "about" is present or not.

Thermal methods are another typical technique to characterize cocrystals. Different cocrystals of the same compound often melt at different temperatures. Variability also exists in thermal measurements, such as DSC, and may also be indicative of sample purity. Melting point, DSC, and hot stage microscopy, alone or in combination with techniques such as x-ray powder diffraction, Raman spectroscopy, infrared spectroscopy or some combination thereof, may be used to characterize cocrystals.

As with any analytical technique, melting point determinations are also subject to variability. Common sources of variability, in addition to instrumental variability, are due to colligative properties such as the presence of other cocrystals or other impurities within a sample whose melting point is being measured.

SUMMARY

In one aspect of the invention, a cocrystal of p-coumaric acid to nicotinamide is disclosed. In another aspect, a cocrystal of p-coumaric acid to nicotinamide in a molar ratio of 1:1 is disclosed. In a further aspect of the invention, a cocrystal of p-coumaric acid to nicotinamide in a molar ratio of 2:1 is disclosed. In further aspects, pharmaceutical compositions comprising the cocrystals described herein are described. In yet further aspects, methods of treating conditions treatable by administration of the cocrystals described herein are disclosed.

DESCRIPTION

In one embodiment of the invention, a cocrystal of p-coumaric acid to nicotinamide in a molar (or molar) ratio of 1:1 (Cocrystal 1) is disclosed. The structure of Cocrystal 1 is set forth in FIG. 1.

Figure 2:
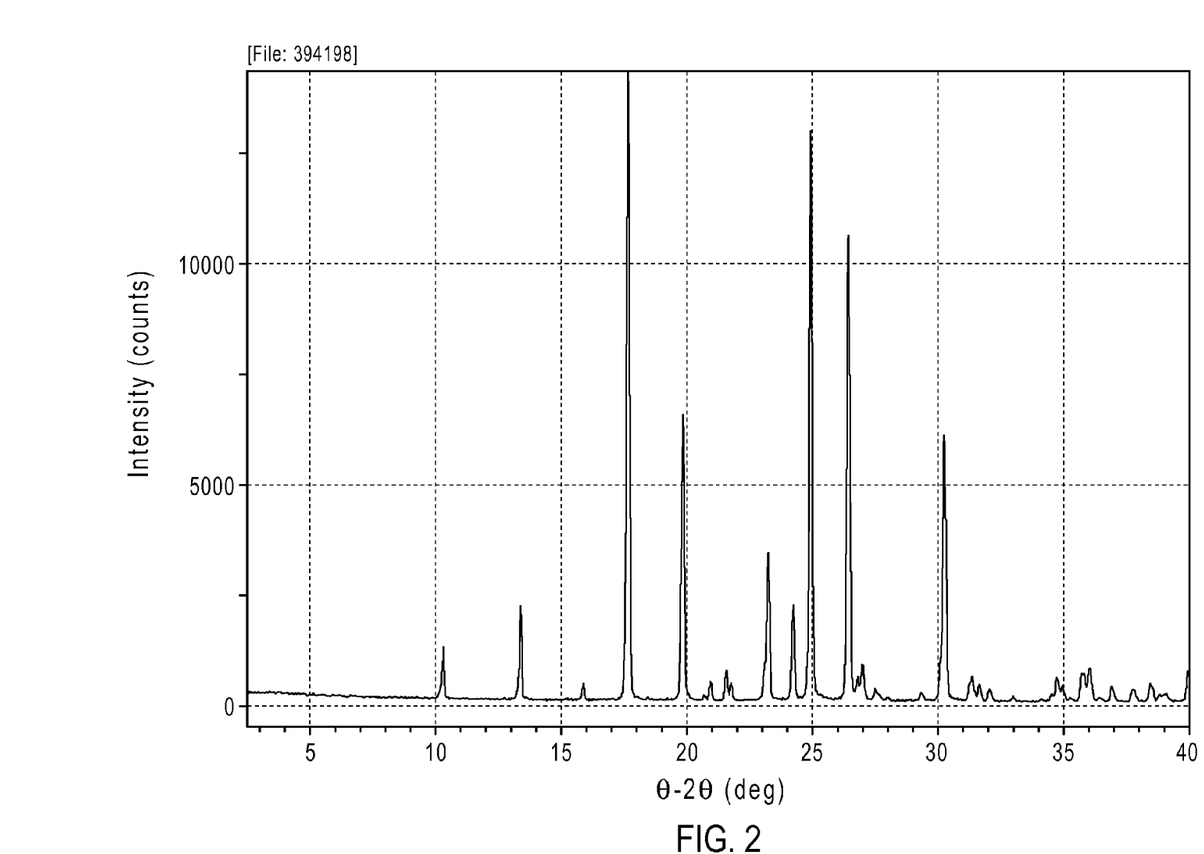
FIG. 2 is an XRPD pattern of p-coumaric acid.

The XRPD pattern corresponding to the p-coumaric acid starting material used herein is in FIG. 2. The XRPD pattern of the nicotinamide starting material is in FIG. 3. The XRPD pattern for the resulting Cocrystal 1 is in FIG. 4.

Figure 1:
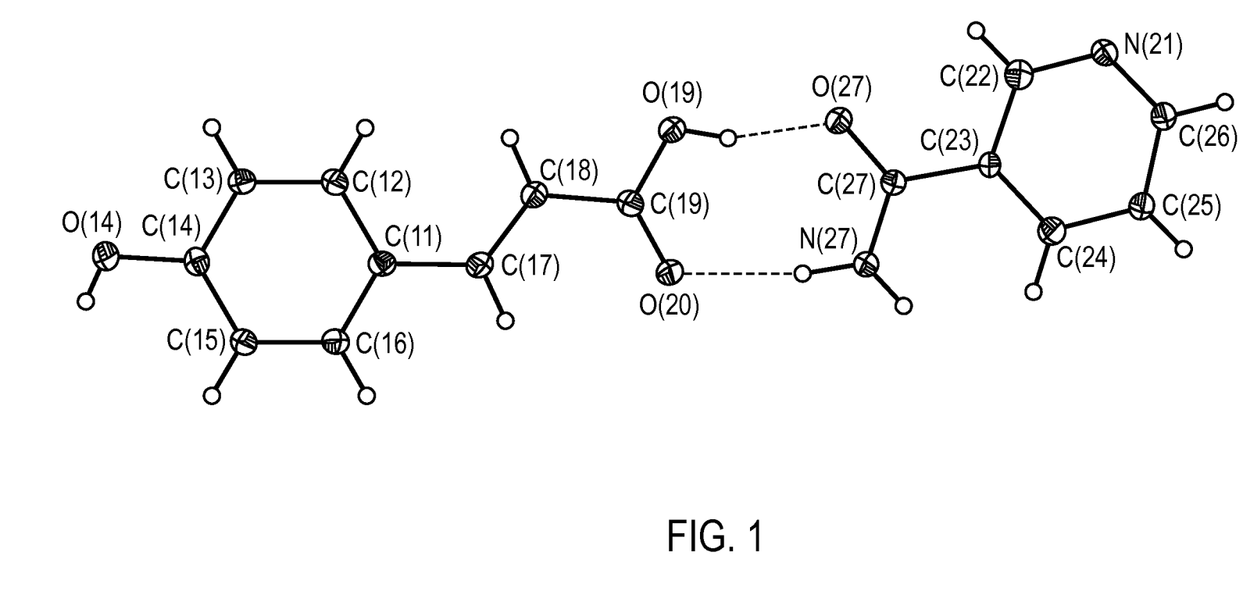
FIG. 1 is a thermal ellipsoid plot of the structure of Cocrystal 1.
Figure 3:
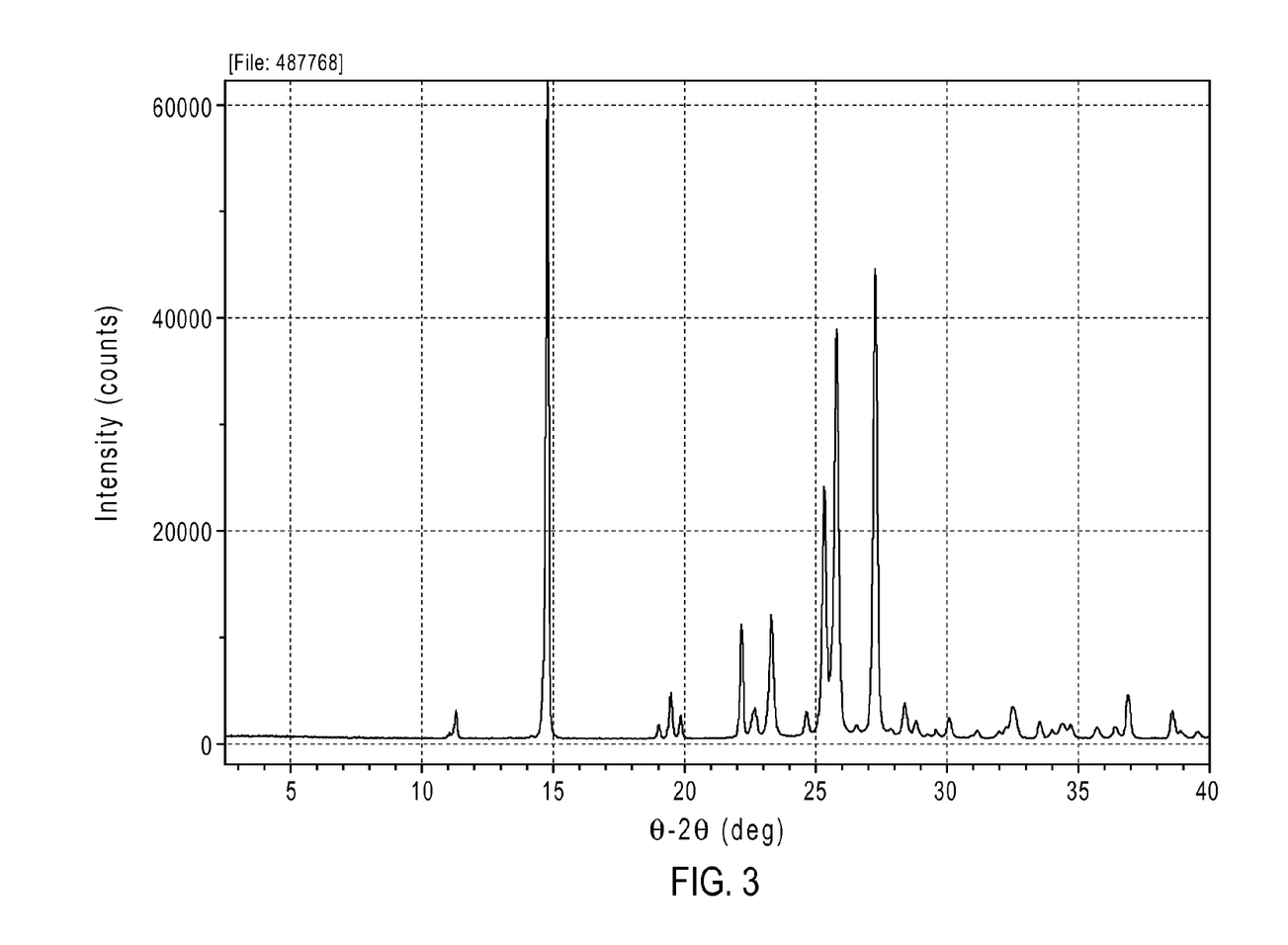
FIG. 3 is an XRPD pattern of nicotinamide.
Figure 4:
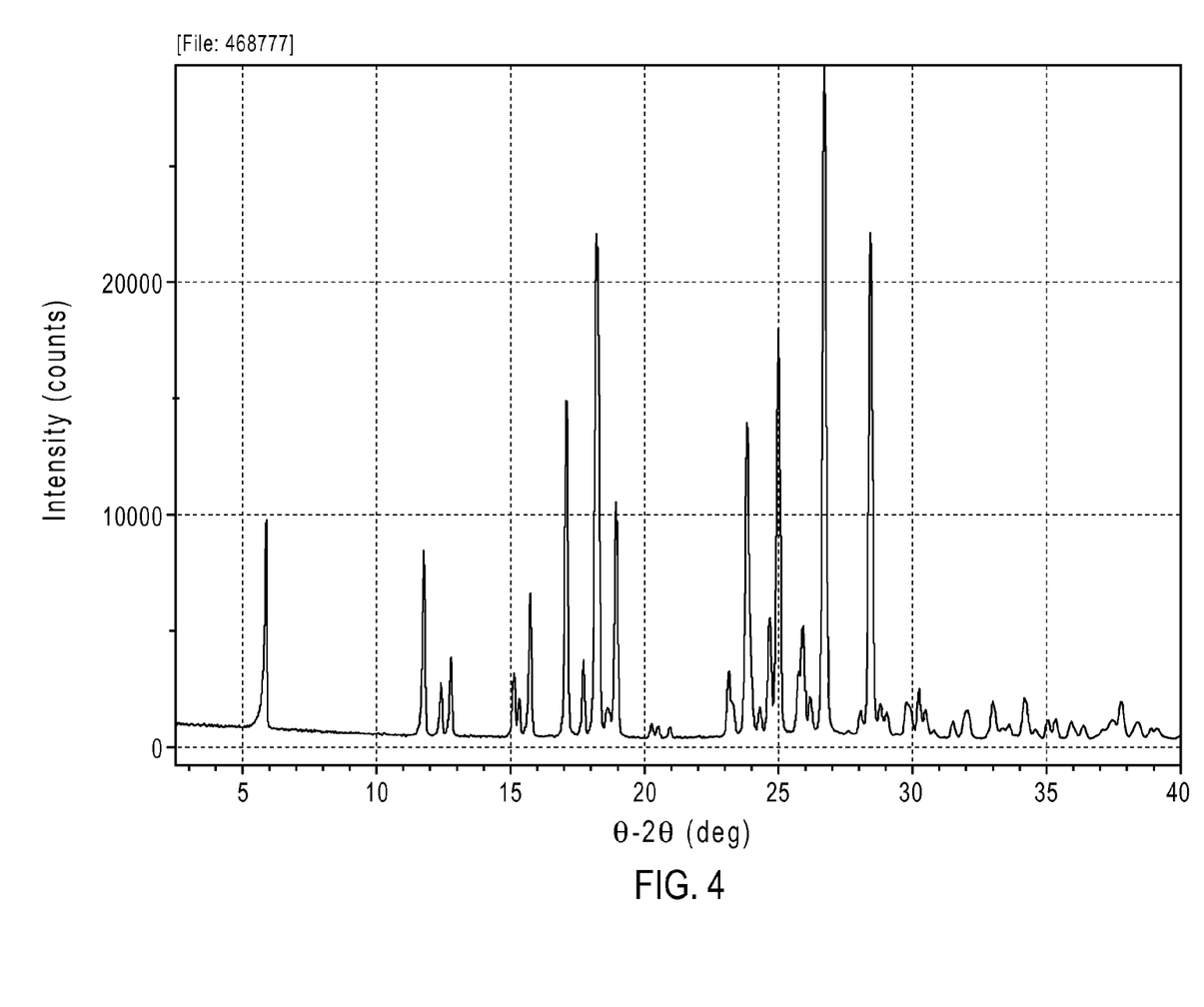
FIG. 4 is an XRPD pattern of Cocrystal 1.

As can be readily determined, the XPRD pattern of FIG. 4 differs from those of FIGS. 2 and 3, and is not merely a linear superposition of the patterns as confirmed by the single crystal structure which is represented in FIG. 1, the parameters for which are set forth in Table 1.

TABLE 1

Crystal data and structure refinement for p-coumaric acid-nicotinamide cocrystal 1:1

| | |
|---|---|
| Identification code | 214544 |
| Empirical formula | C15 H14 N2 O4 |
| Formula weight | 286.28 |
| Temperature | 120(2) K |
| Wavelength | 0.71073 Å |
| Crystal system | Monoclinic |
| Space group | P2(1)/c |
| Unit cell dimensions | a = 15.5106(10) Å   α = 90°. |
| | b = 6.2871(4) Å    β = 106.086(3)°. |
| | c = 14.1238(10) Å  γ = 90°. |
| Volume | 1323.38(15) Å$^3$ |
| Z | 4 |
| Density (calculated) | 1.437 g/cm$^3$ |
| Absorption coefficient | 0.106 mm$^{-1}$ |
| F(000) | 600 |
| Crystal size | 0.34 × 0.18 × 0.10 mm$^3$ |
| Theta range for data collection | 2.73 to 32.58°. |
| Index ranges | −23 <= h <= 23, −9 <= k <= 5, −21 <= l <= 17 |
| Reflections collected | 14583 |
| Independent reflections | 4670 [R(int) = 0.0281] |
| Completeness to theta = 32.58° | 96.8% |
| Absorption correction | None |
| Max. and min. transmission | 0.9895 and 0.9649 |
| Refinement method | Full-matrix least-squares on F$^2$ |
| Data/restraints/parameters | 4670/0/204 |
| Goodness-of-fit on F$^2$ | 1.022 |
| Final R indices [I > 2sigma(I)] | R1 = 0.0461, wR2 = 0.1292 |
| R indices (all data) | R1 = 0.0603, wR2 = 0.1408 |
| Largest diff. peak and hole | 0.534 and −0.252 e.Å$^{-3}$ |

A pattern substantially the same as the pattern of FIG. 4 may be used to characterize Cocrystal 1. A smaller subset of the peaks identified in FIG. 4 may be used to characterize Cocrystal 1. For example, any one or more of the peaks at about 5.9, 11.8, 15.7, 17.1, 18.2, 18.9, 23.8, 25.0, 26.7, or 28.4°2θ may be used to characterize Cocrystal 1.

Figure 5:
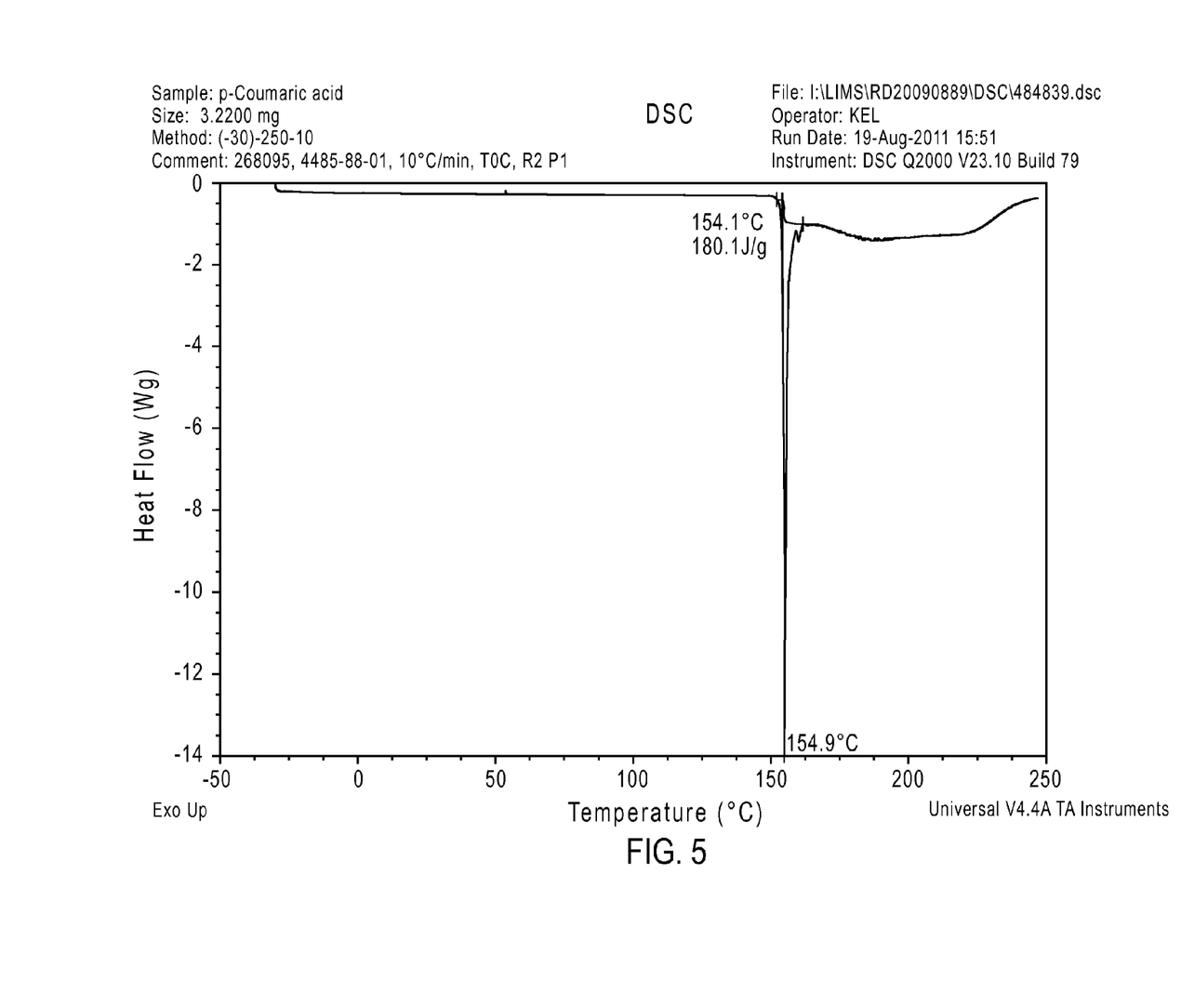
FIG. 5 is a DSC thermogram of Cocrystal 1.

Cocrystal 1 may be characterized by its thermal characteristics. For example, FIG. 5 is a DSC thermogram of Cocrystal 1 and it exhibits an endotherm at about 155° C. under the conditions set forth herein for DSC for the thermogram in FIG. 5. Cocrystal 1 may be characterized by DSC alone or in combination with XRPD diffraction pattern or one or more of the peaks set forth herein.

Figure 6:
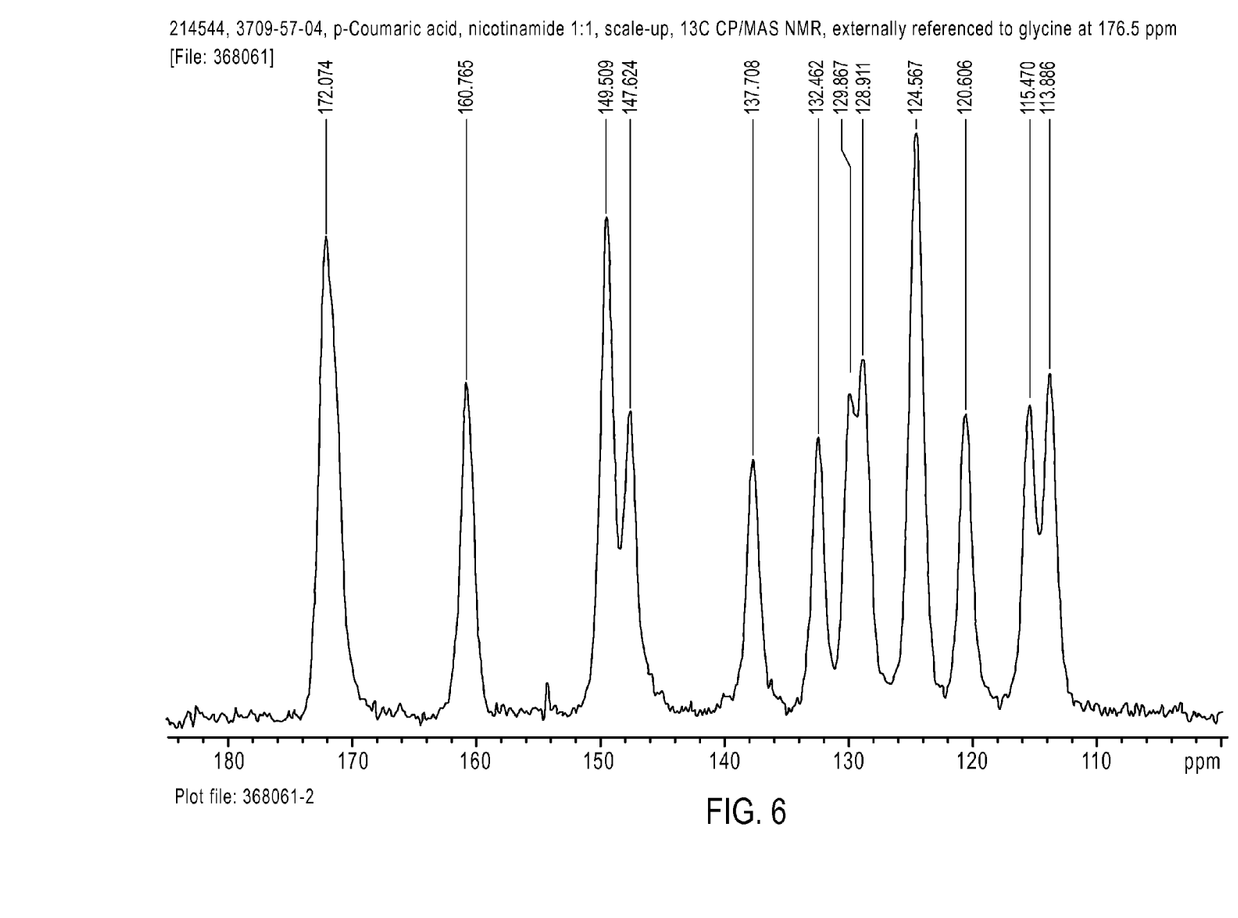
FIG. 6 is a $^{13}$C Solid-State NMR spectrum of Cocrystal 1.

Cocrystal 1 may be characterized by the solid-state $^{13}$C NMR spectrum in FIG. 6. When considering just $^{13}$C solid-state NMR spectroscopy, the entire spectrum may be used to characterize Cocrystal 1 or a subset thereof. For example, any one of the peaks at about 172.1, 160.8, 149.5, 147.6, 137.7, 132.5, 129.9, 128.9, 124.6, 120.6, 115.5, or 113.9 ppm or others may be used alone or in combination to characterize Cocrystal 1.

Cocrystal 1 may be characterized by one or more of the solid-state NMR, DSC, and x-ray techniques as set forth herein. For example, Cocrystal 1 may be characterized by a peak at 5.9°2θ and DSC endotherm of about 155° C. Further, a solid-state NMR peak at about 172.1 ppm may be used to characterize Cocrystal 1.

In another embodiment, the invention is directed to a cocrystal of p-coumaric acid and nicotinamide in a molar ratio of 2:1 (Cocrystal 2).

Figure 7:
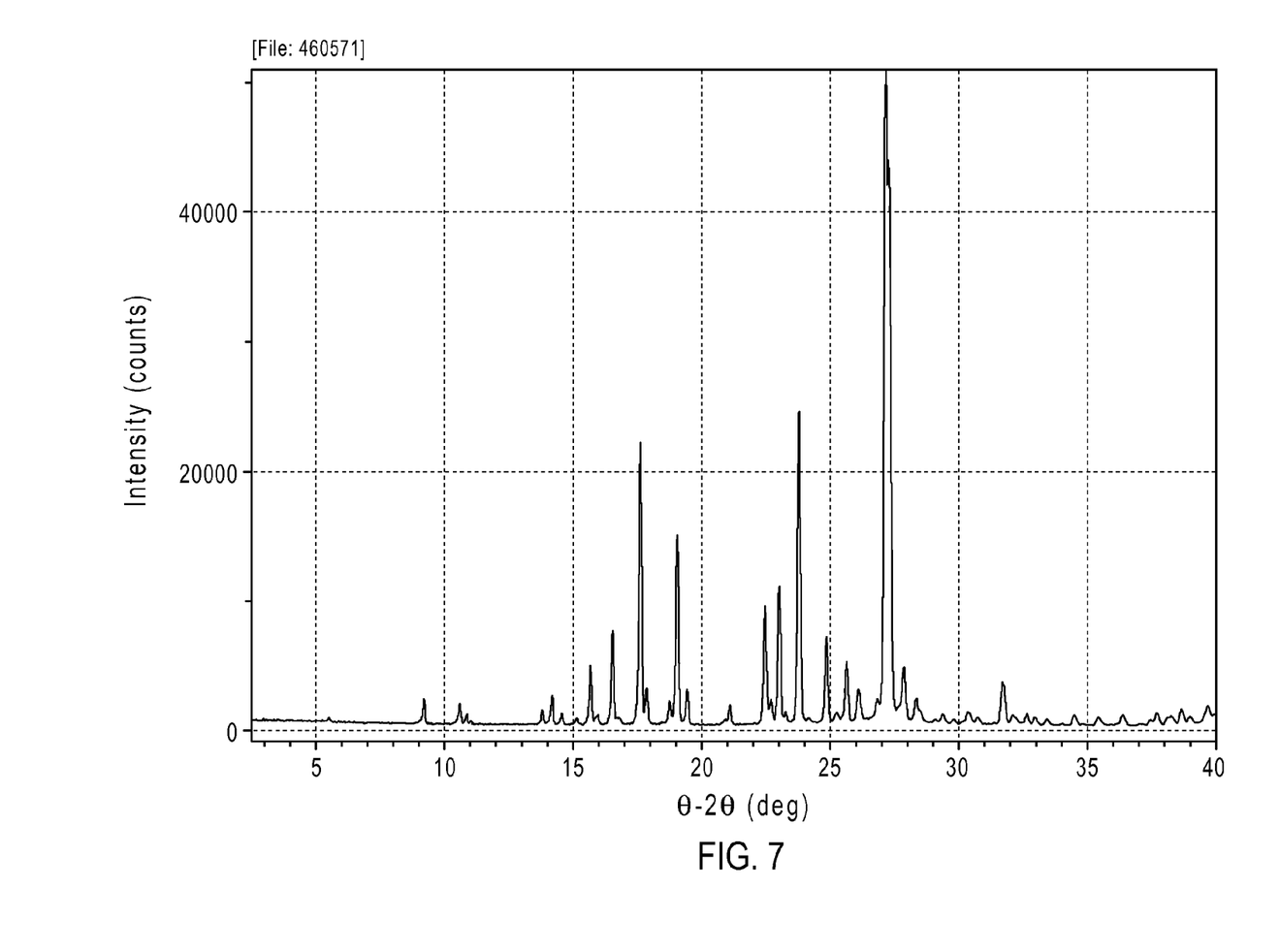
FIG. 7 is an XRPD pattern of Cocrystal 2.

FIG. 7 is the XRPD pattern of Cocrystal 2. As can be readily determined, the XPRD pattern of FIG. 7 differs from those of FIGS. 2 and 3 and is not merely a linear superposition of those patterns, thus, FIG. 7 does not represent a physical mixture. In addition, solution-state 1HNMR of dissolved Cocrystal 2 confirms a molar ratio of 2:1 of p-coumaric acid to nicotinamide.

A pattern substantially the same as the pattern of FIG. 7 may be used to characterize Cocrystal 2. A smaller subset of the peaks identified in FIG. 7 may be used to characterize Cocrystal 2. For example, any one or more of the peaks at about 16.5, 17.6, 19.0, 22.5, 23.0, 23.8, 24.8, 27.1, or 27.3°2θ may be used to characterize Cocrystal 2.

Figure 8:
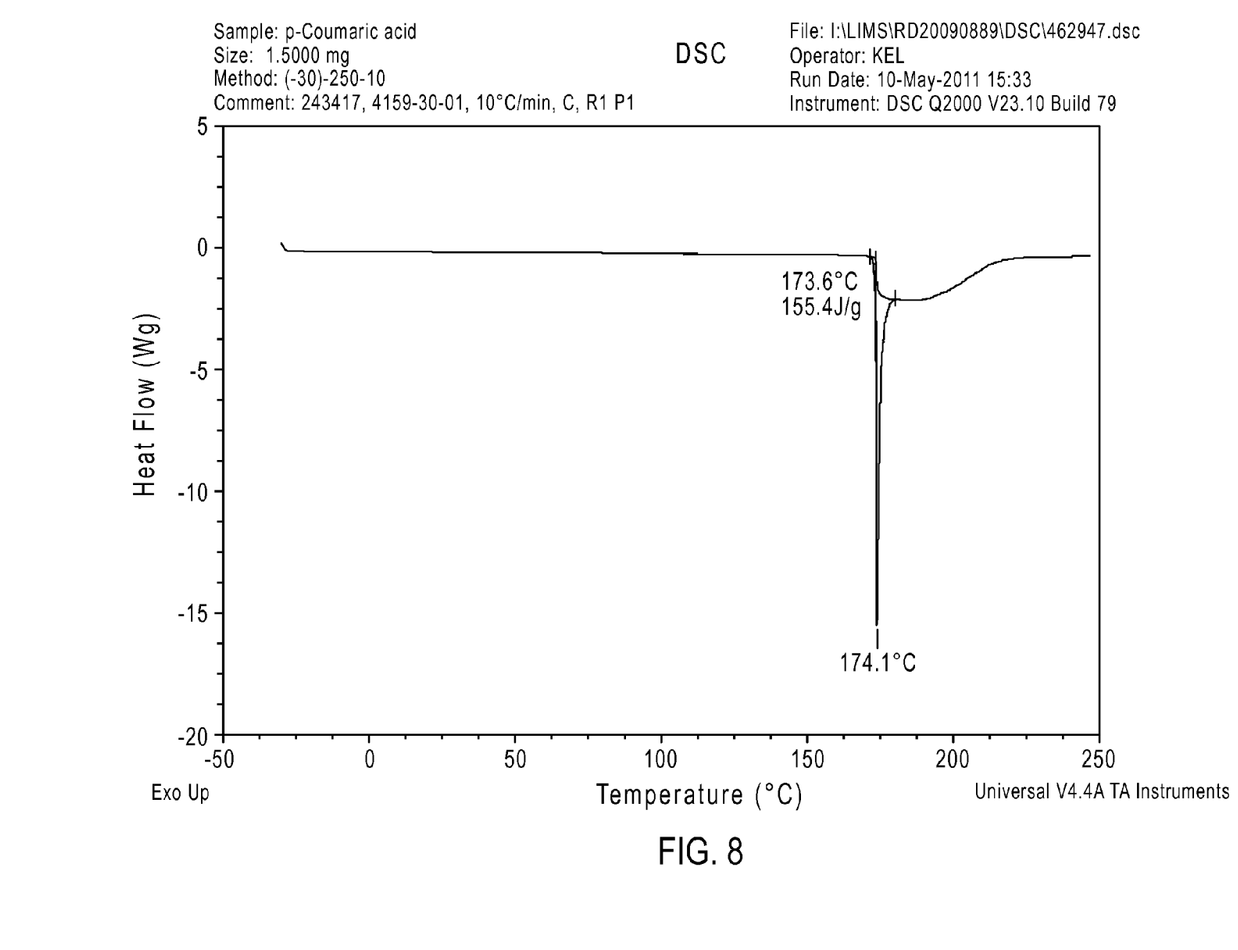
FIG. 8 is a DSC thermogram of Cocrystal 2.

Cocrystal 2 may be characterized by its thermal characteristics. For example, FIG. 8 is a DSC thermogram of Cocrystal 2 and it exhibits an endotherm at about 174° C. under the conditions set forth herein for DSC for the thermogram in FIG. 8. Cocrystal 2 may be characterized by DSC alone or in combination with XRPD diffraction pattern or one or more of the peaks set forth herein.

Figure 9:
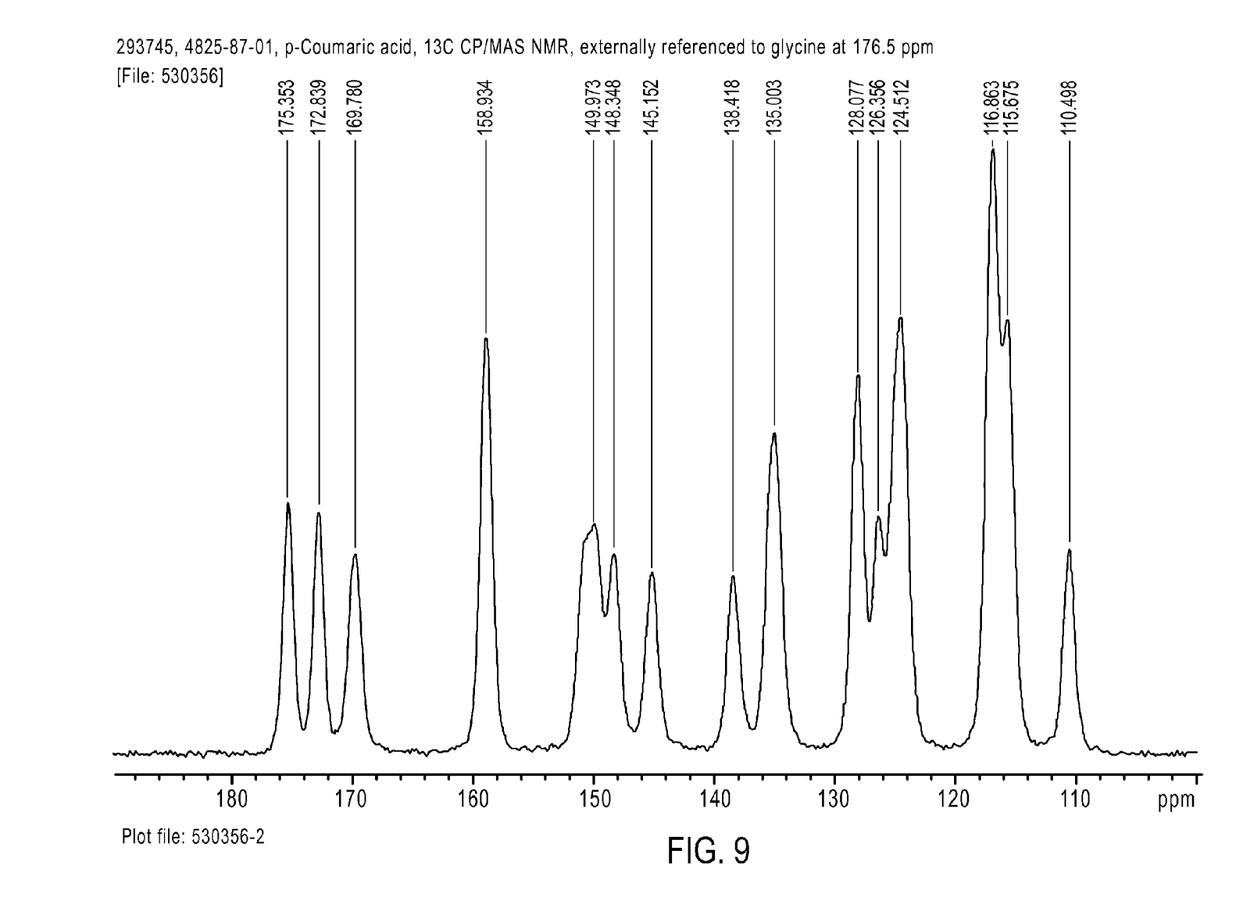
FIG. 9 is a $^{13}$C Solid-State NMR spectrum of Cocrystal 2.

Cocrystal 2 may be characterized by the solid-state spectrum in FIG. 9. When considering just solid-state NMR spectroscopy, the entire spectrum may be used to characterized Cocrystal 2 or a subset thereof. For example, any one of the peaks at about 175.4, 172.8, 169.8, 158.9, 150.0, 148.3, 145.2, 138.4, 135.0, 128.1, 126.4, 124.5, 116.9, 115.7, or 110.5 ppm or others may be used alone or in combination to characterize Cocrystal 2.

Cocrystal 2 may be characterized by one or more of the solid-state NMR, DSC, and x-ray techniques as set forth herein. For example, Cocrystal 2 may be characterized by a peak at 17.6°2θ and DSC endotherm of about 174° C. Further, a solid-state $^{13}C$ NMR peak at About 158.9 ppm may be used to characterize Cocrystal 2.

This invention also relates to pharmaceutical compositions containing cocrystals of the present invention. These compositions can be utilized to achieve the desired pharmacological effect by administration to a patient in need thereof including, treatment of acne or other inflammation conditions. A patient, for the purpose of this invention, is a mammal, including a human, in need of treatment for the particular condition or disease including, but not limited to, acne or other inflammation conditions. Therefore, the present invention includes pharmaceutical compositions which are comprised of at least one pharmaceutically acceptable carrier and a cocrystal of the present invention. A pharmaceutically acceptable carrier is any carrier which is relatively non-toxic and innocuous to a patient at concentrations consistent with effective activity of the active ingredient so that any side effects ascribable to the carrier do not vitiate the beneficial effects of the active ingredient. A pharmaceutically effective amount of compound is that amount which produces a result or exerts an influence on the particular condition being treated. The compound of the cocrystals of the present invention can be administered with pharmaceutically-acceptable carriers well known in the art using any effective conventional dosage unit forms, including immediate, slow and timed release preparations, orally, parenterally, topically, nasally, ophthalmically, optically, sublingually, rectally, vaginally, and the like.

EXAMPLES

All chemicals were obtained from commercial sources and used without further purification.

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-μm-thick films and analyzed in transmission geometry. A beam-stop, short antiscatter extension, antiscatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b.

Solution 1H NMR spectra were acquired at ambient temperature with a Varian UNITYINOVA-400 spectrometer. Samples were dissolved in DMSO-d6 containing TMS. The spectra was referenced to internal tetramethylsilane (TMS) at 0.0 ppm DSC analyses were performed using a TA Instruments 2920 and Q2000 differential scanning calorimeter. Temperature calibration was performed using NIST-traceable indium metal. Samples were placed into an aluminum DSC pan, covered with a lid (T0C—Tzero crimped), and the weight was accurately recorded. A weighed aluminum pan configured as the sample pan was placed on the reference side of the cell. The data acquisition parameters and pan configuration for each thermogram are displayed on images. The method code on the thermogram for each corresponding Figure is an abbreviation for the start and end temperature as well as the heating rate; e.g., −30-250-10 means "from −30° C. to 250° C., at 10° C./min".

The solid-state 13C cross polarization magic angle spinning (CP/MAS) NMR spectra were acquired at ambient temperature on a Varian UNITYINOVA-400 spectrometer (Larmor frequencies: 13C=100.542 or 100.543 MHz, 1H=399.789 or 399.787 MHz). The samples were packed into a 4 mm PENCIL type zirconia rotor and rotated at 12 kHz at the magic angle. The spectra were acquired with phase modulated (TPPM or SPINAL-64) high power 1H decoupling during the acquisition time using a 1H pulse width of 2.9 or 2.6 or 2.6 μs (90°), a ramped amplitude cross polarization contact time of 5 ms, a 30 ms acquisition time, a 120 or 240 second delay between scans, a spectral width of 45 kHz with 2700 data points, and 100, 400, or 1000 co-added scans. The free induction decay (FID) was processed using Varian VNMR 6.1C software with 32768 or 65536 points and an exponential line broadening factor of 10 Hz to improve the signal-to-noise ratio. The first three data points of the FID were back predicted using the VNMR linear prediction algorithm to produce a flat baseline. The chemical shifts of the spectral peaks were externally referenced to the carbonyl carbon resonance of glycine at 176.5 ppm.

Example 1

Cocrystal 1 Preparation 1

Solids of p-coumaric acid and nicotinamide were added to MEK, with an excess of p-coumaric acid, such that undissolved solids remained. The mixture was allowed to stir at ambient temperature for two days, resulting in an opaque white suspension. Solids were collected by vacuum filtration and washed with MEK on the filter.

Example 2

Cocrystal 1 Preparation 2

Weighed amounts of p-coumaric acid (309.3 mg) and nicotinamide (230.3 mg) were added to a clean vial in a 1:1 molar ratio. Ethanol (30 mL) was added with sonication, resulting in a clear solution. The solution was uncapped and covered with perforated aluminum foil for slow evaporation at ambient conditions. After approximately 6 weeks, the sample contained solids with a small amount of solvent remaining. The solids were collected by vacuum filtration, resulting in off-white, rectangular and irregular plates exhibiting birefringence.

Example 3

Cocrystal 2

Weighed amounts of p-coumaric acid (706.1 mg) and nicotinamide (352.3 mg) were combined with MEK (9 mL). The mixture was allowed to stir at ambient temperature for 3 days, and the resulting solids were collected by vacuum filtration. A portion of the solids (245.4 mg) was combined with water (5 mL), and the resulting slurry was allowed to stir at ambient temperature for approximately 8 hours. The solids were collected by vacuum filtration. Water (2 mL) was then added to the resulting solids, and the slurry was allowed to stir at ambient temperature for approximately 3 hours. The resulting solids were collected by vacuum filtration.

What is claimed is:

1. A cocrystal of p-coumaric acid and nicotinamide having a molar ratio of p-coumaric acid to nicotinamide of 2:1 having an x-ray powder diffraction pattern comprising one or more peaks at about 16.5°2θ, about 17.6°2θ, 19.0°2θ, 22.5°2θ, about 23.0°2θ, about 23.8°2θ, about 24.8°2θ, about 27.1°2θ, or about 27.3°2θ.

2. The cocrystal of claim 1 having a DSC thermogram with an endotherm at about 174.1° C.

3. The cocrystal of claim 1 having a $^{13}$C solid-state NMR spectrum comprising one or more peaks at about 175.4 ppm, about 172.8 ppm, about 169.8 ppm, about 158.9 ppm, about 150.0 ppm, about 148.3 ppm, about 145.2 ppm, about 138.4 ppm, about 135.0 ppm, about 128.1 ppm, about 126.4 ppm, about 124.5 ppm, about 116.9 ppm, about 115.7 ppm, or about 110.5 ppm.

4. The cocrystal of claim 2 having a $^{13}$C solid-state NMR spectrum comprising a peak at about 158.9 ppm.

5. A pharmaceutical composition comprising at least one cocrystal of claim 1 and at least one pharmaceutically acceptable carrier.

6. The cocrystal of claim 2 having a $^{13}$C solid state NMR spectrum comprising one or more peaks at about 175.4 ppm, about 172.8 ppm, about 169.8 ppm, about 158.9 ppm, about 150.0 ppm, about 148.3 ppm, about 145.2 ppm, about 138.4 ppm, about 135.0 ppm, about 128.1 ppm, about 126.4 ppm, about 124.5 ppm, about 116.9 ppm, about 115.7 ppm, or about 110.5 ppm..

7. A cocrystal of p-coumaric acid and nicotinamide.

8. The cocrystal of claim 7 having an x-ray powder diffraction pattern comprising one or more peaks at either (i) about 5.9°2θ, about 11.8°2θ, about 15.7°2θ, about 17.1°2θ, about 18.2°2θ, about 18.9°2θ, about 23.8°2θ, about 25.0°2θ, about 26.7°2θ, or about 28.4°2θ or (ii) about 16.5°2θ, about 17.6°2θ, about 19.0°2θ, about 22.5°2θ, about 23.0°2θ, about 23.8°2θ, about 24.8°2θ, about 27.1°2θ, or about 27.3°2θ.

9. The cocrystal of claim 8, wherein the molar ratio of p-cournaric acid to nicotinamide is 2:1.

10. The cocrystal of claim 9 having a DSC thermogram with an endotherm at about 174° C.

11. The cocrystal of claim 9 having a $^{13}$C solid-state NMR spectrum comprising a peak at about 158.9 ppm.

* * * * *

UNITED STATES PATENT AND TRADEMARK OFFICE
CERTIFICATE OF CORRECTION

| | | |
|---|---|---|
| PATENT NO. | : 10,098,859 B2 | Page 1 of 1 |
| APPLICATION NO. | : 14/017879 | |
| DATED | : October 16, 2018 | |
| INVENTOR(S) | : Bevill and Schultheiss | |

It is certified that error appears in the above-identified patent and that said Letters Patent is hereby corrected as shown below:

In the Claims

Claim 9, at Column 8, Line 28, delete "p-cournaric" and insert in its place the word --p-coumaric--.

Signed and Sealed this
Twenty-fifth Day of December, 2018

Andrei Iancu
*Director of the United States Patent and Trademark Office*